United States Patent
Huang

(10) Patent No.: US 10,216,148 B2
(45) Date of Patent: Feb. 26, 2019

(54) WEARABLE DEVICE MADE BY AMORPHOUS ALLOY WITH ANTIBACTERIAL FUNCTION

(71) Applicant: Dongguan Jianye Material Technology Co., Ltd., Dongguan (CN)

(72) Inventor: Limin Huang, Dongguan (CN)

(73) Assignee: DONGGUAN JIANYE MATERIAL TECHNOLOGY CO., LTD., Dongguan (CN)

(*) Notice: Subject to any disclaimer, the term of this patent is extended or adjusted under 35 U.S.C. 154(b) by 0 days.

(21) Appl. No.: 15/717,200

(22) Filed: Sep. 27, 2017

(65) Prior Publication Data

US 2018/0017943 A1     Jan. 18, 2018

(30) Foreign Application Priority Data

Oct. 10, 2016  (CN) .................. 2016 2 1111480 U

(51) Int. Cl.
| | | |
|---|---|---|
| *G04B 37/12* | (2006.01) | |
| *A01N 59/06* | (2006.01) | |
| *A01N 59/16* | (2006.01) | |
| *A01N 59/20* | (2006.01) | |
| *A44C 5/00* | (2006.01) | |
| *A61B 5/024* | (2006.01) | |
| *A61B 5/00* | (2006.01) | |
| *G04G 21/02* | (2010.01) | |
| *G06F 1/16* | (2006.01) | |

(52) U.S. Cl.
CPC ............ *G04B 37/12* (2013.01); *A01N 59/06* (2013.01); *A01N 59/16* (2013.01); *A01N 59/20* (2013.01); *A44C 5/0015* (2013.01); *A44C 5/0023* (2013.01); *A61B 5/02438* (2013.01); *A61B 5/681* (2013.01); *G04G 21/025* (2013.01); *G06F 1/163* (2013.01); *A44C 5/0053* (2013.01); *A61B 2503/10* (2013.01)

(58) Field of Classification Search
CPC ...... G04G 21/025; G06F 1/163; G04B 37/12; A01N 59/06; A01N 59/16; A01N 59/20; A44C 5/0015; A44C 5/0023; A44C 5/0053; A61B 5/02438; A61B 5/681; A61B 2503/10
See application file for complete search history.

(56) References Cited

U.S. PATENT DOCUMENTS 7,396,595 B2 *  7/2008  Shibuya ............... A44C 27/006
                                                              428/660
7,412,848 B2 *  8/2008  Johnson ............... A44C 27/002
                                                              63/23

(Continued)

*Primary Examiner* — Sean P Kayes
(74) *Attorney, Agent, or Firm* — Shimokaji IP

(57) ABSTRACT

A wearable device made by amorphous alloy with antibacterial function includes a functional part adapted for implementing using functions of the wearable device; and an amorphous alloy housing configured out of the functional part and adapted for cladding the functional part to prevent the functional part from directly contacting with a user. Since the wearable device has the amorphous alloy housing covering on the functional part, thus the amorphous alloy housing rather than the functional part will contact with the user skin directly. As the amorphous alloy has excellent bactericidal capability, thus user wearing such a wearable device will get a good user experience.

7 Claims, 2 Drawing Sheets

(56) References Cited

U.S. PATENT DOCUMENTS

| | | | |
|---|---|---|---|
| 7,622,198 B2 * | 11/2009 | Miya | A44C 27/005 428/213 |
| 9,207,644 B2 * | 12/2015 | Bazin | B21J 1/006 |
| 9,933,754 B2 * | 4/2018 | Dubach | G04B 37/22 |
| 2004/0231159 A1 * | 11/2004 | Shibuya | A44C 27/006 29/896.412 |
| 2016/0103428 A1 * | 4/2016 | Fujisawa | G04R 60/12 368/28 |

* cited by examiner

WEARABLE DEVICE MADE BY AMORPHOUS ALLOY WITH ANTIBACTERIAL FUNCTION

CROSS-REFERENCE TO RELATED APPLICATIONS

This application claims the benefit of priority to Chinese Invention Application No. 201621111480.X, filed Oct. 10, 2016, which is hereby incorporated by reference in its entirety.

FIELD OF THE INVENTION

The invention relates to a technical field of amorphous material, and more particularly to amorphous alloy with antibacterial function.

BACKGROUND OF THE INVENTION

Amorphous alloy is molten metal obtained by quenching the metal alloy, and its microstructure is different from the crystalline metal, with short-range order, long-range disorder characteristics, so that the surface of the amorphous alloy has many empty electron orbits, the surface electron coordination is unsaturated and the surface free energy is higher than that of the crystalline alloy, therefore it is under unstable state or metastable state thermodynamically, and will be transformed into crystalline structure in certain condition.

Based on a variety of excellent mechanical, physical and chemical properties, the amorphous alloy is widely used in the field of aerospace, but the use in the civilian field is insufficient.

Therefore, there is a need for providing a civilian product made by amorphous alloy to improve the increasing material needs of people.

SUMMARY OF THE INVENTION

One objective of the present invention is to provide a civilian product made by amorphous alloy to improve the increasing material needs of people.

To achieve the above-mentioned objective, the present invention provides a wearable device made by amorphous alloy with antibacterial function, which includes a functional part, adapted for implementing using functions of the wearable device; and an amorphous alloy housing, configured out of the functional part and adapted for cladding the functional part to prevent the functional part from directly contacting with a user.

In comparison with the prior art, since the wearable device of the present invention has the amorphous alloy housing covering on the functional part, thus the amorphous alloy housing rather than the functional part will contact with the user skin directly. As the amorphous alloy has excellent bactericidal capability, thus user wearing such a wearable device will get a good user experience.

Preferably, the wearable device is a sport watch, a sport bracelet, a heart rate testing band, or a health monitoring bracelet.

Preferably, the functional part comprises a CPU, a testing part and a communication transmission structure.

Preferably, the amorphous alloy housing is made of amorphous alloy by means of molding process or machining process.

Preferably, the amorphous alloy housing comprises a housing and an amorphous alloy layer which is coated on an outer side of the housing by spraying, sputtering, or plating.

Preferably, the amorphous alloy layer is formed on a side of the housing that is facing to the user.

Preferably, the amorphous alloy housing is made of metal material or plastic material.

Specifically, the amorphous alloy with antibacterial function has the following compositions: Ag 2 wt %~8 wt %; Eu 1 wt %~3 wt %; Ce 1 wt %~3 wt %; Mg 20 wt %~40 wt %; Cu 40 wt %~60 wt %; Zn 3 wt %~10 wt %; and Al 1 wt %~5 wt %. Such an amorphous alloy made by these metals is antibacterial and bactericidal. "Antibacterial" function means that, at proliferation stage of bacteria, these metals are absorbed on the cytoderm and combined with the cytomembrane, thus the enzyme in the cytomembrane will be destroyed to prevent electron transport of energy metabolism required by cell growth, thereby inhibiting bacterial individual growth. "Bactericidal" function means that, at non-proliferation stage of bacteria, these metals destroys the enzyme in the cytomembrane to kill the bacteria due to normal energy metabolism required by cell growth is inhibited.

Ag has the strongest bactericidal capability, while Ce and Eu are active metals in the rare-earth elements, which are served as alloy additive to improve the bactericidal capability of the alloy. That's because Ag, Ce and Eu show synergistic antibacterial activity, and can contact with cytomembrane by electric field adsorption to destroy sheath structure and wall structure of the bacterial, thereby improving bactericidal effect of the amorphous alloy regarding to *staphylococcus aureus* and *escherichia coli*, and achieving sterilization rate up to 99.99 wt %. Furthermore, the alloy has excellent photostability.

Advantages of the prevent invention includes: broad-spectrum antibacterial property to resist *escherichia coli*, *staphylococcus aureus*, or *pseudomonas aeruginosa*, etc.; high safety with low toxicity, nonirritant to skin, and being not teratogenic and not carcinogenic; good thermostability; strong persistence with slow release property; small drug resistance; and low volatilization to prevent environment.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The present invention is directed to a wearable device that is made by amorphous alloy with antibacterial function, so as to improve use experience and meet the user demand. The wearable device can be a sport watch, a sport bracelet, a heart rate testing band, or a health monitoring bracelet, etc.

The amorphous alloy with antibacterial function has the following compositions: Ag 2 wt %~8 wt %; Eu 1 wt %~3 wt %; Ce 1 wt %~3 wt %; Mg 20 wt %~40 wt %; Cu 40 wt %~60 wt %; Zn 3 wt %~10 wt %; and Al 1 wt %~5 wt %. Such an amorphous alloy made by these metals is antibacterial and bactericidal. "Antibacterial" function means that, at proliferation stage of bacteria, these metals are absorbed on the cytoderm and combined with the cytomembrane, thus the enzyme in the cytomembrane will be destroyed to prevent electron transport of energy metabolism required by cell growth, thereby inhibiting bacterial individual growth. "Bactericidal" function means that, at non-proliferation stage of bacteria, these metals destroys the enzyme in the cytomembrane to kill the bacteria due to normal energy metabolism required by cell growth is inhibited.

Therein, Ag has the strongest bactericidal capability, while Ce and Eu are active metals in the rare-earth elements, which are served as alloy additive to improve the bactericidal capability of the alloy. That's because Ag, Ce and Eu show synergistic antibacterial activity, and can contact with cytomembrane by electric field adsorption to destroy sheath structure and wall structure of the bacterial, thereby improving bactericidal effect of the amorphous alloy regarding to *staphylococcus aureus* and *escherichia coli*, and achieving sterilization rate up to 99.99 wt %. Furthermore, the alloy has excellent photo stability.

Figure 1:
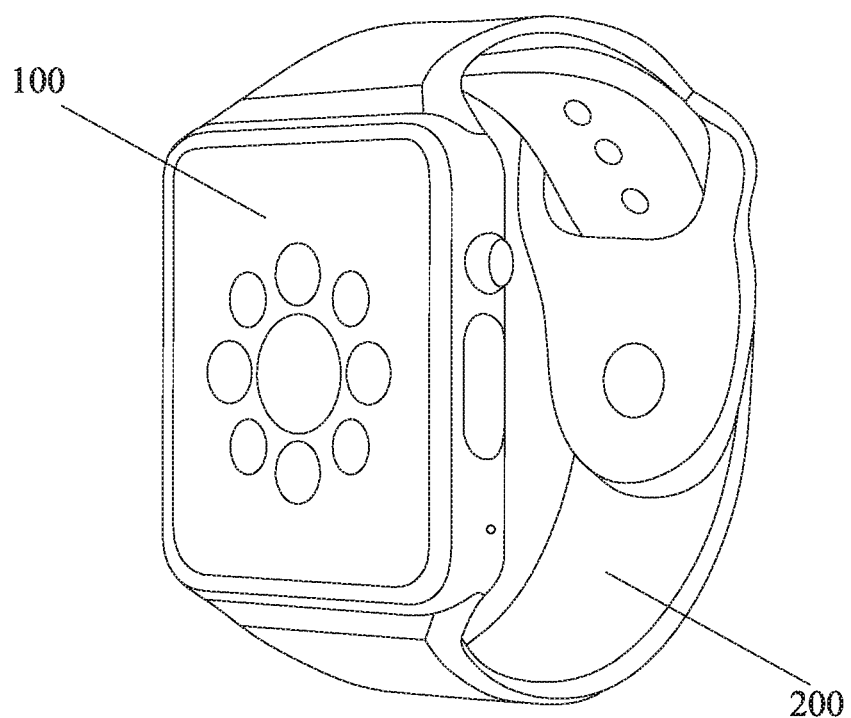
FIG. 1 is a perspective view of a sport watch made of amorphous alloy according to the present invention.

For example, as shown in FIG. 1 of a sport watch that is made of amorphous alloy with antibacterial function, the sport watch includes a functional part 100 and an amorphous alloy housing 200 configured out of the functional part 100 and adapted for cladding the functional part 100. Specifically, the functional part 100 is adapted for implementing using functions of the wearable device, and the amorphous alloy housing 200 is adapted for preventing the functional part 100 from directly contact with the user.

Specifically, the functional part includes a CPU, a testing part and a communication transmission structure, which are connected and assembled together with other necessary components according to common manners skilled in the art to achieve necessary functions of sport watch including timing, speed measurement, heart rate measurement and data transmission, etc., in this embodiment. In other embodiments, other functional modules also can be set, such as heart rate monitoring module or blood pressure monitoring module, etc.

The amorphous alloy housing 200 is made of the amorphous alloy mentioned above, especially the side of the housing 200 that is facing to user skin is formed by amorphous alloy material, and thus the housing 200 is antibacterial.

Figure 2:
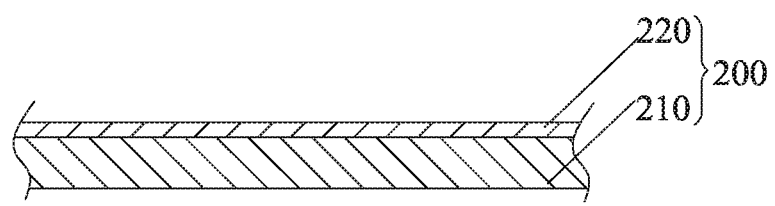
FIG. 2 is a sectional view of the amorphous alloy housing according to a first embodiment of the present invention.

FIG. 2 is a sectional view of the amorphous alloy housing 200 according to a first embodiment of the present invention. Specifically, the amorphous alloy housing 200 includes a housing 210 and an amorphous alloy layer 220 which is coated on an outer side of the housing 210 by spraying, sputtering, or plating. In such a way, less amorphous alloy material is required to reduce manufacturing cost and obtain good usage experience.

Furthermore, the amorphous alloy layer 220 is formed on a side of the housing 200 that is facing to the user. In such a way, the appearance of the wearable device will not be affected, and further, less amorphous alloy material is required, instead of covering the whole of the housing with amorphous alloy material.

Figure 3:
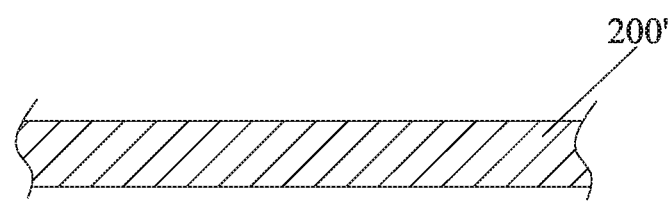
FIG. 3 is a sectional view of the amorphous alloy housing according to a second embodiment of the present invention.

Differing from the FIG. 2, FIG. 3 shows sectional view of the amorphous alloy housing 200 according to a second embodiment of the present invention. The amorphous alloy housing 200 is made of amorphous alloy by means of molding process or machining process. Since the amorphous alloy has bactericidal capability, thus the housing 200 made by amorphous alloy also has good bactericidal capability.

In comparison with prior arts, since the wearable device of the present invention has the amorphous alloy housing 200 covering on the functional part 100, thus the amorphous alloy housing 200 rather than the functional part 100 will contact with the user skin directly. As the amorphous alloy has excellent bactericidal capability, thus user wearing such a wearable device will get a good user experience. Alternatively, the whole of the amorphous alloy housing 200 may be made by amorphous alloy to obtain the excellent user experience; or merely the surface of the housing 210, especially that surface facing to the user skin is made by amorphous alloy to form the amorphous alloy layer 220, thereby reducing manufacturing cost and meanwhile keeping the good bactericidal capability.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. A wearable device made by amorphous alloy with antibacterial function, comprising:
    a functional part, adapted for implementing using functions of the wearable device; and
    an amorphous alloy housing, configured out of the functional part and adapted for cladding the functional part to prevent the functional part from directly contacting with a user, wherein the amorphous alloy housing includes an amorphous alloy layer which comprises below compositions: Ag 2 wt %~8 wt %; Eu 1 wt %~3 wt %; Ce 1 wt %~3 wt %; Mg 20 wt %~40 wt %; Cu 40 wt %~60 wt %; Zn 3 wt %~10 wt %; and Al 1 wt %~5 wt %.

2. The wearable device according to claim 1, wherein the wearable device is a sport watch, a sport bracelet, a heart rate testing band, or a health monitoring bracelet.

3. The wearable device according to claim 2, wherein the functional part comprises a CPU, a testing part and a communication transmission structure.

4. The wearable device according to claim 1, wherein the amorphous alloy housing is made of amorphous alloy by means of molding process or machining process.

5. The wearable device according to claim 1, wherein the amorphous alloy housing comprises a housing and the amorphous alloy layer which is coated on an outer side of the housing by spraying, sputtering, or plating.

6. The wearable device according to claim 5, wherein the amorphous alloy layer is formed on a side of the housing that is facing to the user.

7. The wearable device according to claim 5, wherein the housing of the amorphous alloy housing is made of metal material or plastic material.

* * * * *